(12) United States Patent
Chapal et al.

(10) Patent No.: US 11,044,930 B2
(45) Date of Patent: Jun. 29, 2021

(54) COMPOSITION COMPRISING CINNAMON EXTRACT

(71) Applicant: NATUREX, Avignon (FR)

(72) Inventors: Nicolas Chapal, Combaillaux (FR); Vickram Beejmohun, Montpellier (FR)

(73) Assignee: NATUREX, Avignon (FR)

( * ) Notice: Subject to any disclaimer, the term of this patent is extended or adjusted under 35 U.S.C. 154(b) by 246 days.

(21) Appl. No.: 16/103,493

(22) Filed: Aug. 14, 2018

(65) Prior Publication Data

US 2018/0343906 A1    Dec. 6, 2018

Related U.S. Application Data

(62) Division of application No. 13/996,987, filed as application No. PCT/EP2011/073932 on Dec. 23, 2011, now Pat. No. 10,076,128.

(30) Foreign Application Priority Data

Dec. 23, 2010  (EP) ..................................... 10306499

(51) Int. Cl.
   *A23L 27/10* (2016.01)
   *A61K 36/54* (2006.01)
   *A23L 33/105* (2016.01)

(52) U.S. Cl.
   CPC .............. *A23L 27/10* (2016.08); *A23L 27/11* (2016.08); *A23L 33/105* (2016.08); *A61K 36/54* (2013.01); *A61K 2236/00* (2013.01)

(58) Field of Classification Search
   None
   See application file for complete search history.

(56) References Cited

U.S. PATENT DOCUMENTS

| | | |
|---|---|---|
| 6,200,569 B1 | 3/2001 | Cheng |
| 7,534,454 B2 | 5/2009 | Karerat et al. |
| 2009/0304827 A1 | 12/2009 | Kim |
| 2011/0052736 A1 | 3/2011 | Romero et al. |

FOREIGN PATENT DOCUMENTS

| | | |
|---|---|---|
| EP | 1 350 516 A1 | 10/2003 |
| EP | 1 640 015 A2 | 3/2006 |
| WO | WO 2008/041049 A1 | 4/2008 |

OTHER PUBLICATIONS

English translation of Koch (EP 1640015) 2006.*
Hlevowicz (Am J Clin Nutr (2007), vol. 85, pp. 1552-1556).*
Jenkins et al., "Relationship Between Rate of Digestion of Foods and Post-Prandial Glycaemia", Diabetologia, vol. 22, 1982, pp. 450-455.
Kar et al., "Comparative evaluation of hypoglycaemic activity of some Indian medicinal plants in alloxan diabetic rats", Journal of Ethnopharmacology, vol. 84, 2003, pp. 105-108, XP-002442210.
Ponnusamy et al., "Evaluation of Traditional Indian Antidiabetic Medicinal Plants for Human Pancreatic Amylase Inhibitory Effect In Vitro", Evidence-Based Complementary and Alternative Medicine, vol. 2011, Article ID 515647, 2011, pp. 1-10, XP009148637.
Shihabudeen et al., "Cinnamon extract inhibits α-glucosidase activity and dampens postprandial glucose excursion in diabetic rats", Nutrition & Metabolism, vol. 8, No. 46, 2011, pp. 1-22, XP-002676701.
Khan, "Muheet-e-Azam vol. III", 1887, pp. 4-7, Matba Nizam, Knapur, India.
Pandita, "Hariprapanna Ji", Rasayoga Sagara, vol. II, 1998, pp. 8-14, Krishnadas Academy, Varanasi, India.
Therayar, "Therayar Karisal", 1st Edition, 1931, pp. 15-19, Viveka Vilakka Press, Chennai, India.

* cited by examiner

*Primary Examiner* — Susan Hoffman
(74) *Attorney, Agent, or Firm* — Birch, Stewart, Kolasch & Birch, LLP

(57) ABSTRACT

The invention concerns a composition for lowering the glycemic index comprising, or consisting of an alcoholic extract of *cinnamon* in an amount of at least 10% by weight compared to the total weight of the composition, and optionally a carrier, a food composition comprising a composition for lowering the glycemic index in an amount ranging from 0.1% to 5% by weight compared to the total weight of the food composition, the use of a composition for lowering the glycemic index or of a food composition as a glycemic index lowering agent.

12 Claims, 8 Drawing Sheets

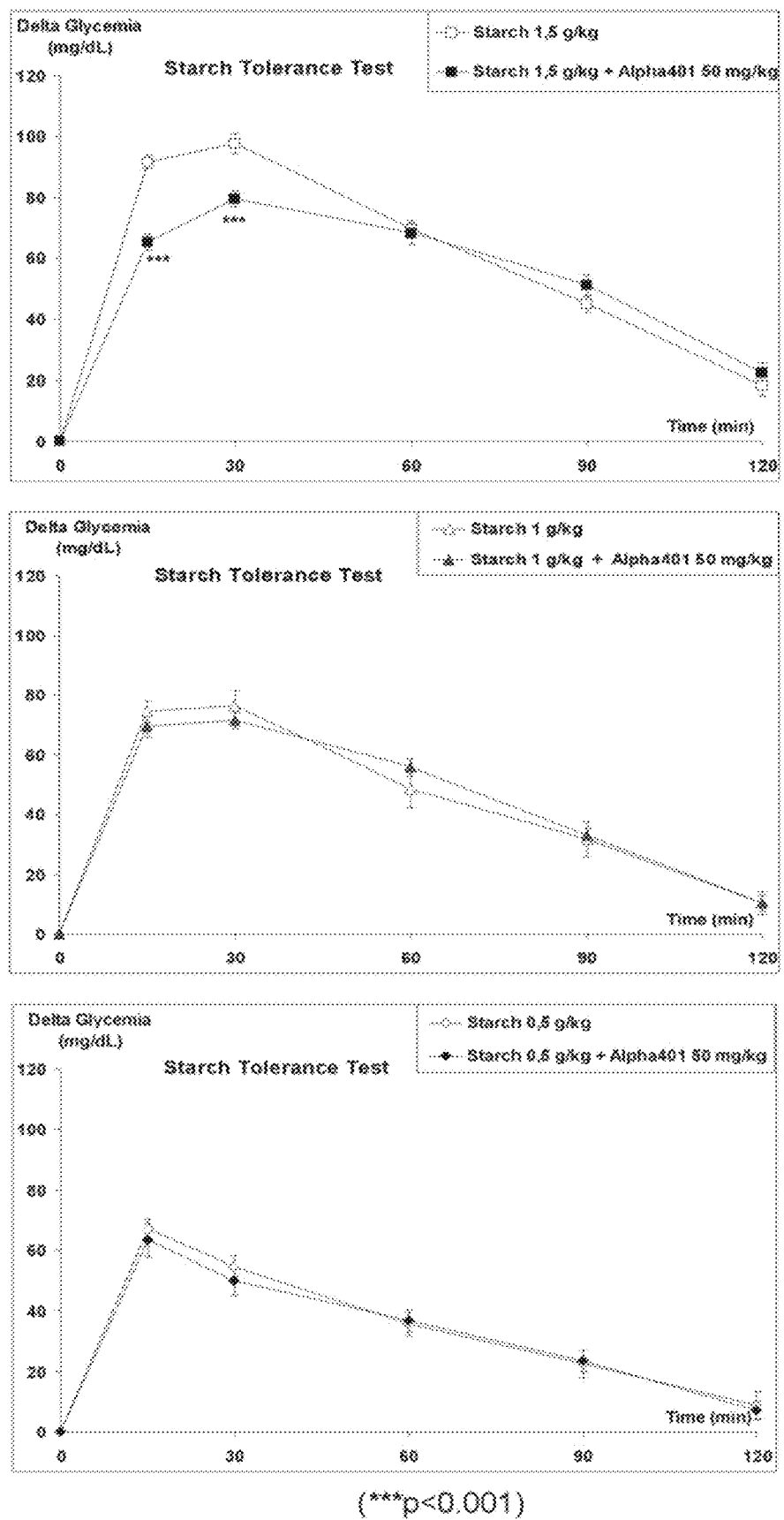
Figure 3: Effect dependant of the quantity of starch

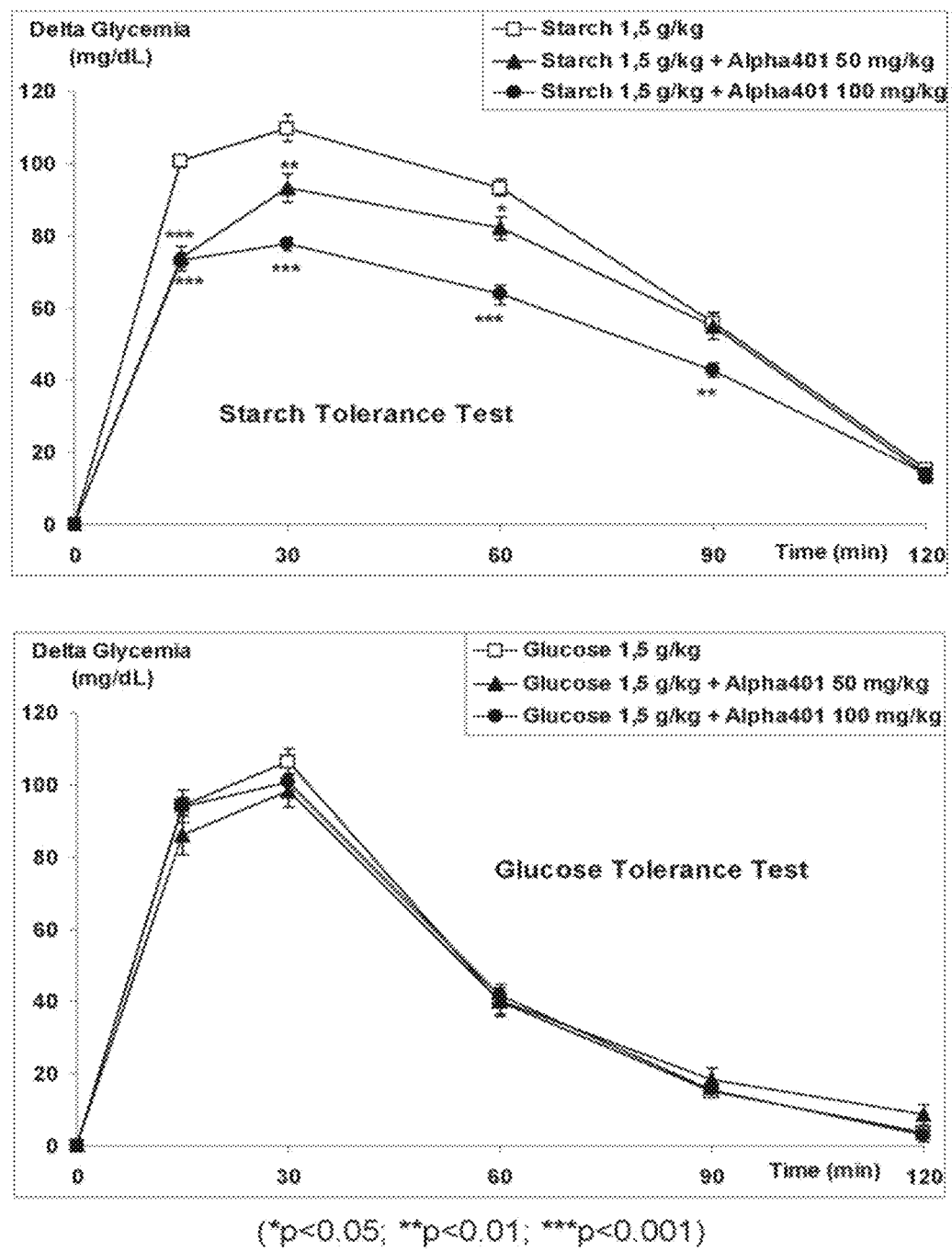
Figure 4: Specific effect on starch versus glucose

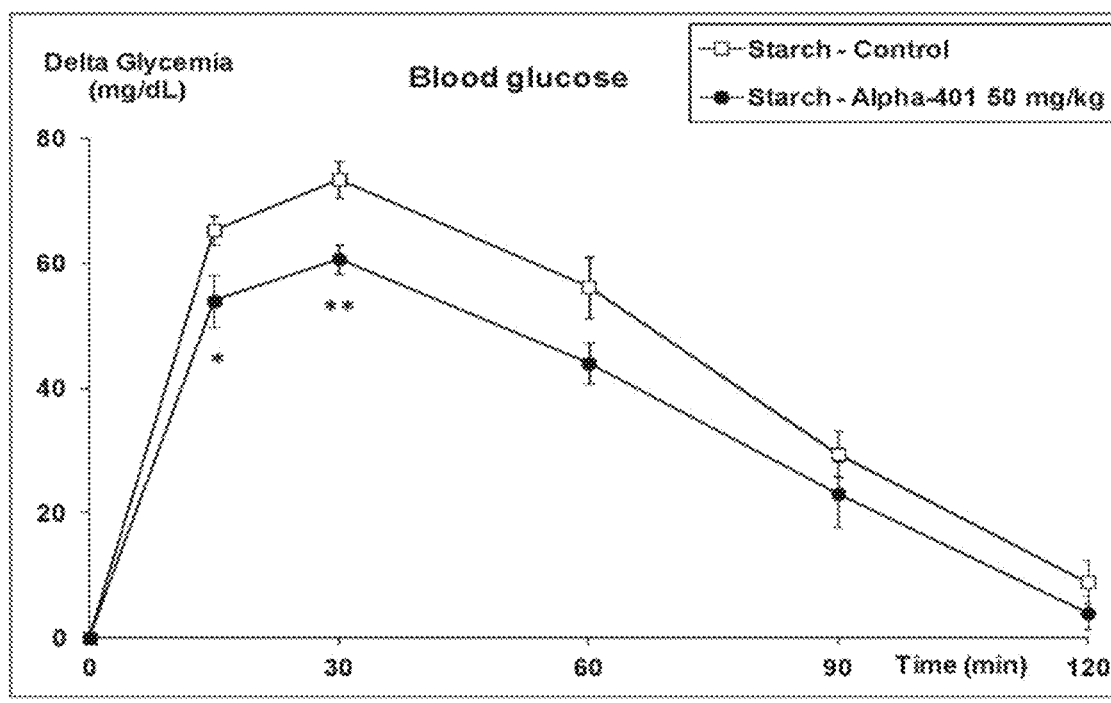
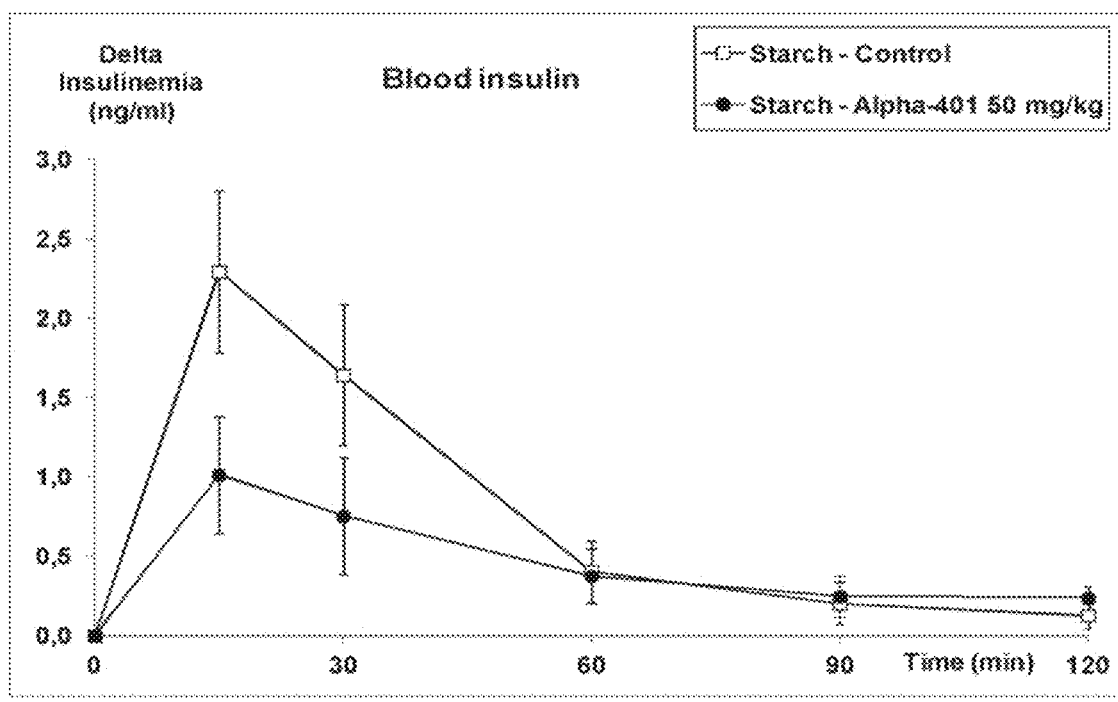
Figure 5: Effect on insulinic response to starch

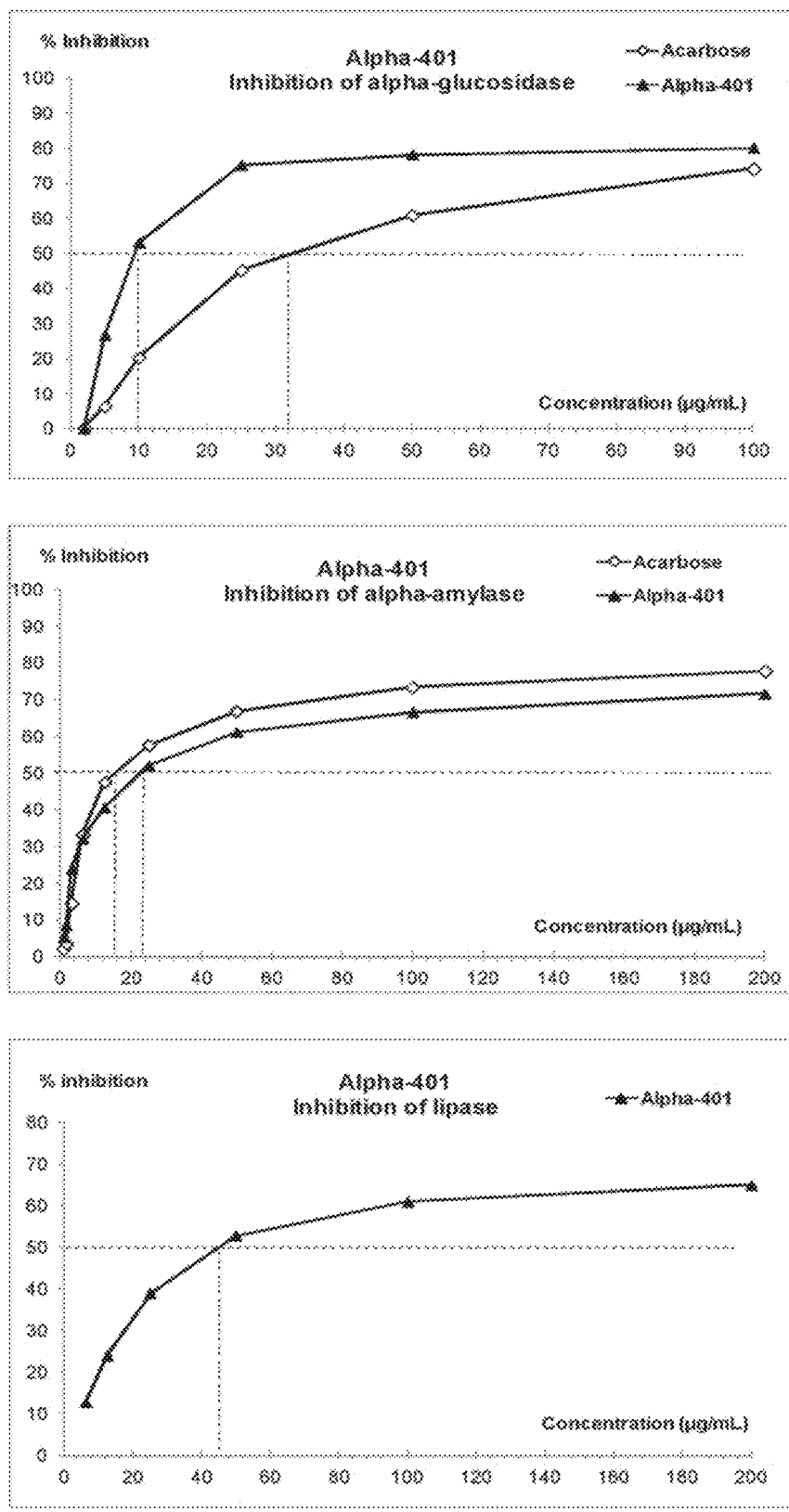
Figure 6: Effect on digestion enzymes

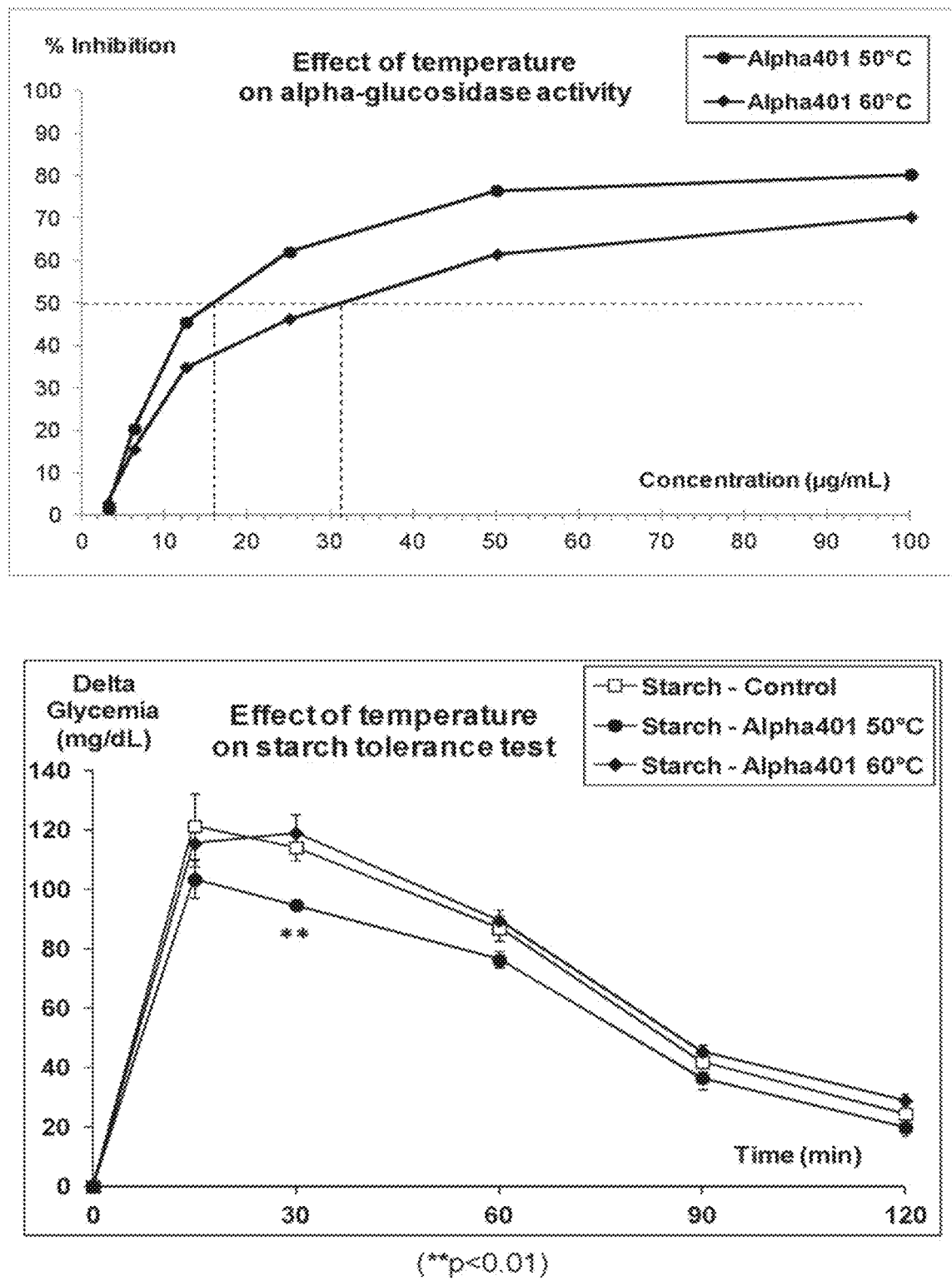
Figure 7: Effect of temperature on cinnamon extract

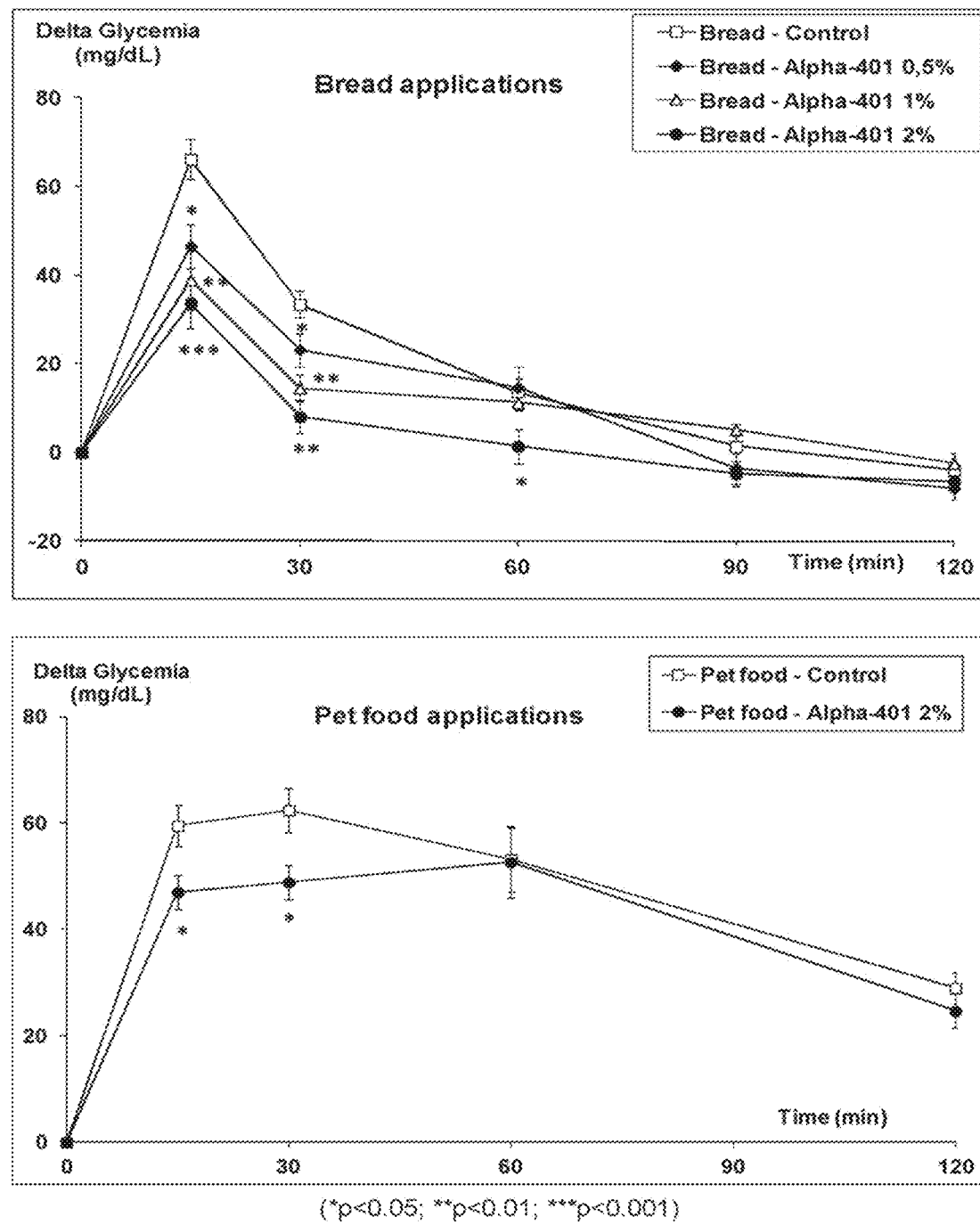
Figure 8: Effect of cinnamon extract incorporated in food matrixes

COMPOSITION COMPRISING CINNAMON EXTRACT

CROSS-REFERENCE TO RELATED APPLICATIONS

This application is a Divisional of U.S. application Ser. No. 13/996,987, filed on Jun. 21, 2013, now U.S. Pat. No. 10,076,128, which is the National Phase of PCT International Application No. PCT/EP2011/073932, filed on Dec. 23, 2011, which claims priority under 35 U.S.C. § 119(a) to application Ser. No. 10/306,499.4, filed in Europe on Dec. 23, 2010, all of which are hereby expressly incorporated by reference into the present application.

The present invention relates to a composition for lowering glycemic index and to low-glycemic index food.

BACKGROUND OF THE INVENTION

The Body Mass Index (BMI) has a tendency to increase, either with human beings or with animals. When the BMI is too high it may cause problems to the subject. Among these problems may be cited health problem, in particular joint problem, diabetes, etc, social problems, such as discrimination, and/or displacement problems. This BMI may be reduced with a diet having a low glycemic index.

The glycemic index, glycemic index, or GI is a measure of the effects of carbohydrates on blood sugar levels. Carbohydrates that break down quickly during digestion and release glucose rapidly into the bloodstream have a high GI; carbohydrates that break down more slowly, releasing glucose more gradually into the bloodstream, have a low GI. The glycemic index is also useful for providing a direct measure of the insulin response to a food. Additionally, investigations indicate that consumption of low-GI carbohydrates may delay the return of hunger and reduce subsequent energy intake relative to consumption of higher-GI carbohydrates. Thus, lowering the glycemic index of food may improve satiety regulation and prevent energy drop associated with blood sugar variation due to food intake.

Regulation of blood sugar variations due to carbohydrate intake may also be useful for purposes distinct from health issues. For example, such regulation could be useful in weight management strategies, to delay the return of hunger. Blood sugar variations also affect athletes and their performance, as carbohydrates usually form a major part of their diet. Athletes may for example benefit from a low GI pre-event meal to avoid reactive hypoglycemia or blood sugar drop. When blood sugar levels spike because of high-glycemic carbohydrates consumption, the release of insulin is over-stimulated. This causes a rapid blood sugar drop. When involved in an aggressive workout or competition, blood sugar might then drop into the hypoglycemic levels.

Particularly in prevision of unusual endurance sessions, where practical difficulties prevent the athlete from consuming carbohydrate supplements during the session, a pre-event meal comprising low glycemic index food permits the slower absorption and release of glucose theoretically sustaining blood glucose and thus enhancing performance.

The occurrence of diabetes and cardiovascular diseases have been strongly correlated with the presence of a combination of medical disorders called metabolic syndrome or metabolic syndrome X, cardiometabolic syndrome, syndrome X, insulin resistance syndrome, Reaven's syndrome. The metabolic syndrome can be defined according to the WHO criteria by the presence of:

one of:
Diabetes mellitus,
Impaired glucose tolerance,
Impaired fasting glucose or
Insulin resistance;
AND two of the following:
Blood pressure: ≥140/90 mmHg
Dyslipidemia: triglycerides (TG): ≥1.695 mmol/L and high-density lipoprotein cholesterol (HDL-C)≤0.9 mmol/L (male), ≤1.0 mmol/L (female)
Central obesity: waist/hip ratio>0.90 (male); >0.85 (female), or body mass index>30 kg/m2
Microalbuminuria: urinary albumin excretion ratio≥20 µg/min or albumin:creatinine ratio≥30 mg/g.

The International Diabetes Federation also proposed a consensus worldwide definition of the metabolic syndrome:
Central obesity (defined as waist circumference #with ethnicity specific values)
AND any two of the following:
Raised triglycerides: >150 mg/dL (1.7 mmol/L), or specific treatment for this lipid abnormality.
Reduced HDL cholesterol: <40 mg/dL (1.03 mmol/L) in males, <50 mg/dL (1.29 mmol/L) in females, or specific treatment for this lipid abnormality
Raised blood pressure: systolic BP>130 or diastolic BP>85 mm Hg, or treatment of previously diagnosed hypertension.
Raised fasting plasma glucose: (FPG)>100 mg/dL (5.6 mmol/L), or previously diagnosed type 2 diabetes. If FPG>5.6 mmol/L or 100 mg/dL, OGTT Glucose tolerance test is strongly recommended but is not necessary to define presence of the Syndrome.

If BMI is >30 kg/m$^2$, central obesity can be assumed and waist circumference does not need to be measured.

Central adiposity is a key feature of the syndrome, reflecting the fact that the syndrome's prevalence is driven by the strong relationship between waist circumference and increasing adiposity. However, despite the importance of obesity, patients that are of normal weight may also be insulin-resistant and have the syndrome. Besides, the prevalence of the metabolic syndrome is strongly correlated to metabolic issues, particularly relating to sugar metabolism issues, and as such to blood glucose variations.

According to many surveys a huge number of people are strongly suspected to be diabetic patient or are undeniable to be diabetic patient. This may amount to 10 to 15% among countries.

The reasons for the increase in the number of diabetic patients may be divided into genetic factors and "living habits" such as obesity, hyperphagia, lack of exercise, and irregular lifestyle. The number of diabetic patients caused by the latter reasons tends to increase. The mechanism of the onset may be that in the case of hyposecretion of insulin associated with postprandial hyperglycemia, or when insulin is secreted but shows resistance and does not work as a hormone, disordered saccharometabolism takes place, which results in diabetes.

Therefore, diet regimen which limits the carbohydrates from meal or pharmacotherapy such as a sugar absorption inhibitor is used for metabolizing sugar with limited insulin.

Some studies showed that normalization of blood glucose over a period of 24 hours may be essential for the onset and development of diabetic angiopathy. Thus, the concept of a glycemic index of foods has been introduced by Jenkins et al. in 1982 (see, for example, Jenkins D J, Ghafari H, Wolever T M, Taylor R H, Jenkins A L, Barker H M, Fielden H, Bowling A C: Relationship between rate of digestion of foods and post-prandial glycaemia, Diabetologia, Vol. 22, 450-455 (1982)).

A glycemic index of a food refers to an index showing the magnitude of the peak of blood glucose level which elevates when the food is ingested. Generally, the glycemic index is obtained by indexation of change of blood glucose level after ingesting various foods as compared with the blood glucose level after ingesting glucose, when the index of any of glucose, polished rice and bread is defined as 100.

It may be considered that when the glycemic index of a food to be ingested is controlled, thereby reducing the load on pancreas, the onset of diabetes can be prevented.

Although some low glycemic index food and/or agent are known in the art, they may need the processing of the foods therefore leading to a huge increase of the cost. They may also have a problem that the forms of the foods are limited, that the agent limiting the glycemic index is highly viscous, which may render difficult the addition of the agent to an ordinary food or to process this agent.

Agents limiting or decreasing the glycemic index may thus be expensive, insufficiently efficient, not versatile enough, not natural, having an appearance or a flavour which is undesirable for the subject, and/or having undesirable effects, for example such as gastric troubles, more particularly flatulence.

The invention thus aims to solve all or part of the above cited problems.

SUMMARY OF THE INVENTION

The present invention provides for an extract of *cinnamomum zeylanicum*, susceptible of being obtained by the process comprising the following steps:
a) contacting dried milled *cinnamomum zeylanicum* bark with an extraction solvent at a temperature of around 50° C.,
b) filtering out the solids and collecting alcoholic extract
c) washing said solids by stirring with an extraction solvent
d) filtering out the solids and collecting alcoholic extract
e) combining said alcoholic extracts
f) removing non-soluble residues by decantation or filtration
g) evaporating the solvents from the combination at a temperature inferior or equal to 50° C.
h) recovering a dry extract The invention also concerns a composition, particularly a food composition comprising an extract of *cinnamomum zeylanicum* of the invention or obtained with a process of the invention.

The invention also concerns the extract or composition of the invention for use as glycemic index lowering agent.

The invention also concerns the extract or composition of the invention for use as weight management agent.

The invention also concerns the extract or composition of the invention for use as satiety regulation agent.

The invention also concerns the extract or composition of the invention for use as workout supplement. The invention also concerns a method to avoid sugar drop in a subject comprising administering to said subject an effective amounts of an extract of the invention.

The subject can be a human being or any other animal, preferably mammal. The animal is preferably a pet, and can be chosen for example among asses, for example mules or donkeys, but also cats, dogs, horses, pigs, guinea pigs, rats, mice, rabbits, gerbils, hamsters, chinchillas, fancy rats.

The invention also concerns a method for regulating satiety in a subject comprising administering to said subject an effective amounts of an extract of the invention.

The invention also concerns a method for preventing or reducing hyperglycaemia in a subject comprising administering to said subject an effective amounts of an extract of the invention.

The invention also concerns a method for preventing obesity or diabetes in a subject comprising administering to said subject an effective amounts of an extract of the invention.

The invention also concerns a process for obtaining *cinnamomum zeylanicum* extract comprising the following steps:
a) contacting dried milled *cinnamomum zeylanicum* bark with an extraction solvent comprising water and an alcoholic solvent.
b) filtering out the solids and collecting the solvent extract
c) optionally, washing said solids by stirring with extraction solvent
d) optionally, filtering out the solids and collecting the solvent extract
e) combining solvent extracts
f) removing non-soluble residues
g) concentrating the solvents
h) evaporating the solvents
i) recovering a dry extract
characterised in that all the steps a) to h) are conducted at a temperature equal or below 50° C.

According to another aspect, the invention has for subject matter a composition for lowering the glycemic index, in particular the glycemic effect of starch, comprising an alcoholic extract of *cinnamon zeylanicum* in an amount of at least 10% by weight compared to the total weight of the composition.

According to another aspect, the invention has for subject matter low-glycemic index food comprising an alcoholic extract of *cinnamon*, in particular *cinnamomum zeylanicum*, or a composition for lowering glycemic index.

According to still another aspect, the invention has for subject matter a diet comprising an oral taking of a composition according to the invention prior or at the same time than the meal or at least 1, 2 or 3 times a day.

DETAILED DESCRIPTION OF THE INVENTION

Thus, following a first aspect, the invention concerns an extract of *cinnamomum zeylanicum*, susceptible of being obtained by the process comprising the following steps:
a) contacting dried milled *cinnamomum zeylanicum* bark with an extraction solvent at a temperature of around 50° C.,
b) filtering out the solids and collecting alcoholic extract
c) washing said solids by stirring with an extraction solvent
d) filtering out the solids and collecting alcoholic extract
e) combining said alcoholic extracts
f) removing non-soluble residues by decantation or filtration
g) evaporating the solvents from the combination at a temperature inferior or equal to 50° C.
h) recovering a dry extract The extract of the invention generally comprises at least 25% by weight of polyphenols and/or at least 40% by weight of polyphenols.

The invention also concerns a composition for lowering the glycemic index comprising, or consisting of an alcoholic extract of *cinnamon*, in particular *cinnamomum zeylanicum*, in an amount of at least 10% by weight compared to the total weight of the composition, and optionally a carrier, in particular a consumable carrier and/or a flavour agent.

The invention also concerns a composition for use a weight management agent, comprising an extract of *cinnamon*.

The invention additionally concerns a composition for use a satiety agent, comprising an extract of *cinnamon*.

The invention also concerns a composition for use a workout supplement, comprising an extract of *cinnamon*.

The *cinnamon* extract may come from the bark of the *cinnamon*, in particular of *cinnamomum zeylanicum*, in an amount of at least 75% by weight, in particular at least 90% by weight, more particularly at least 95% by weight compared to the total weight of the *cinnamon* extract.

Following an embodiment, 100% of the *cinnamon*, in particular the *cinnamomum zeylanicum*, extract is coming from the bark.

In particular the composition comprises at least 10% by weigh, more particularly at least 25% by weight, even more particularly at least 50% by weight, still more particularly at least 75% by weight of the alcoholic extract compared to the total weight of the composition.

The composition may comprise an amount of *cinnamon* extract going from 10 to 99% by weight, more particularly from 25 to 95% by weight, even more particularly from 50 to 95% by weight, still more particularly from 75 to 95% by weight of the alcoholic extract compared to the total weight of the composition.

The extract may comprise at least 25% by weight, in particular at least 30% by weight, and more particularly at least 35% by weight of polyphenols compared to the total weight of the extract.

The composition may comprise at least 10% by weight, in particular at least 20% by weight, more particularly at least 30% by weight, still more particularly at least 35% by weight of polyphenols compared to the total weight of the composition.

By "polyphenols" is meant chemical substances found in plants, characterized by the presence of more than one phenol group per molecule.

The polyphenols may comprise, or consists of catechins, polymeric polyphenol compounds and mixtures thereof.

In a specific embodiment, the amount of coumarin present in the extract of *cinnamon* is lower or equal to 200 ppm by weight, in particular to 180 ppm by weight, more particularly to 150 ppm by weight, and even more particularly to 120 ppm by weight compared to the total weight of the extract.

Thus the amount of coumarin present in the composition may be lower or equal to 200 ppm by weight, in particular to 180 ppm by weight, more particularly to 150 ppm by weight, and even more particularly to 120 ppm by weight compared to the total weight of the composition.

The amount of coumarin may be measured by High-Performance Liquid Chromatography (HPLC).

The composition may comprise an amount of coumarin such that the amount of delivered to the subject is less than or equal to 0.1 mg/kg/day, in particular less or equal to 0.75 mg/k/day.

The extraction solvent, for obtaining the *cinnamon* extract, comprises, or consist of, at least one alcohol chosen from methanol, ethanol, n-propanol, iso-propanol, 2-butanol, ter-butanol, in particular ethanol, and optionally water, in particular in an amount of 5 to 80%, more particularly of 5 to 50%, by weight compared to the total weight of the extraction solvent.

More particularly, the solvent comprises, or consists, of at least 50% by weight, in particular at least 65% by weight and still more particularly at least 75% by weight of alcohol, in particular ethanol, and optionally water, in particular to complete to 100% by weight.

Following an embodiment, the composition for lowering the glycemic index is a liquid, in particular intended to be drunken before meal.

The alcoholic *cinnamon* extracts may be prepared by various methods.

*Cinnamon* extracts may be obtained by a process comprising the following steps:
  a) Contacting dried milled *cinnamomum zeylanicum* bark with an extraction solvent; and
  b) filtering out the solids and collecting the solvent extract
  c) optionally, washing said solids by stirring with extraction solvent
  d) optionally, filtering out the solids and collecting the solvent extract
  e) combining solvent extracts
  f) removing non-soluble residues
  g) concentrating the solvents
  h) evaporating the solvents
  i) recovering a dry extract
  All the steps (steps a) to h)) of the extraction process of the invention are preferably conducted at a temperature below 80° C., more preferably conducted at a temperature equal or below 50° C.

Extraction in step 1 is advantageously performed at a temperature above 30° C., particularly above 40° C., more particularly around 50° C. Around 50° C. is defined as being 50° C.±5° C.

The solvent of the extraction process are preferably chosen among organic solvents, more preferably alcoholic solvents, soluble in water and combinations thereof. Among the alcoholic solvents may be cited ethanol.

Suitable solvents may be chosen from water, methanol, ethanol, n-propanol, iso-propanol, 2-butanol, and combinations thereof.

More particularly the extraction solvent comprises at least 50%, at least 65%, more particularly at least 75%, and even more particularly at least 100% by weight of organic solvent compared to the total weight of the extraction solvent, and still more particularly consists of such solvent(s).

Following an embodiment, the extraction is performed with water and/or an alcoholic solvent, in particular ethanol.

In case of an extraction performed with water and alcohol, in particular ethanol, the weight ratio water/alcohol may range from 5/95 to 50/50, and even more particularly is of around 50/50.

The extract being obtain may be qualified to be aqueous, alcoholic, or organic solvent extracts.

The percentage of alcohol, and in particular ethanol, used for extraction can have an impact on the yield and composition of the biologically active compounds.

The extraction may be done by batch or continuously, or by successive uses of a same extraction solvent in successive batches to obtain saturation of the solvent with the extract. For batch extraction, the person skilled in the art shall define appropriate weight ratio solvent/solid parts of the plant, optimized for an industrial process. The ratio solvent/solid ratio may be ranging from 2 to 20, in particular 5 to 15 and more particularly around 10 times the weight of solids. The extraction may be done one or several time, in particular 2 to 4 times.

Low ratios may be used in continuous or successive batch extraction processes.

The extraction may be performed at a temperature ranging from 30 to 80° C., in particular above 40° C., and more particularly around 50° C.

The extraction may last from 1 to 5 hours, in particular around 2 hours, under stirring, for example mechanical or magnetic stirring.

The remaining solids may be filtered out, in particular through a filter bag.

Several extracts may be combined to form a single extract according to the invention.

The wet solids may be extracted another time by further stirring with a solvent, in particular a hydro-alcoholic mixture, with a volume from 1 to 100 times the weight of the dry solids, and a stirring for about 10 to 120 minutes, particularly 15 to 30 minutes.

The solids are collected and the extracts may be combined.

The different extraction solutions may be combined.

Non-soluble residues may be removed by decantation, filtration through filter paper or centrifugation.

The clear supernatants obtained may be concentrated to about 5% to 20% of their initial volume, for example using a concentrator, and may be then treated with food grade alcohol, in particular ethanol, in a definite proportion, for example a minimum of 2 times the concentrated volume, to remove any precipitate formed. This step may allow removing all or parts of undesired compounds, such as polysaccharides or water soluble proteins.

A powdered extract may be obtained by drying the concentrated extracts, for example using spray drier, oven at 50-80° C., preferably around 50° C., or vacuum drier, preferably around 50° C.

In particular the extract may be obtained by a process comprising the following steps:

1) contacting dried milled *cinnamon*, in particular *cinnamomum zeylanicum*, bark with 3 to 25 times, in particular around 10 times, more particularly around 7 times, their weight with an extraction solvent such as disclosed above, in particular a mixture ethanol-water comprising at least 50% by weight of ethanol, and more particularly a mixture ethanol-water having a 1/1 weight ratio, and agitating, for example for 2 hours, at a temperature above 30° C., more particularly above 40° C., and still more particularly of around 50° C.,
2) the solids are filtered out and the alcoholic extract is collected,
3) the wet solid is washed by stirring with extraction solvent, in particular with a volume corresponding to 1 to 100 times the weight of the dry solids, for example for about 15 to 30 minutes, more preferably for 30 to 120 minutes,
4) the solid are filtered out and the alcoholic extract collected,
5) the extraction solutions are combined and left for decantation or filtered to remove non-soluble residues,
6) the solvents of alcoholic solution are concentrated to about 5% to 20% of their initial volume for example using a concentrator under reduced pressure thus leading to a brown syrup, and the concentrate may be evaporated, for example by staying in an oven at 50-80° C. dried, more preferably at 50° C., or under vacuum, for example with vacuum spray drying, particularly at 50° C., or frozen for lyophilisation
7) dry extract is recovered.

In particular the solutions are, and in particular the final solution is not overheated, for example at more than 80° C. or boiled. More particularly the solution is not heated over 50° C. It may deteriorate some compounds of the extract, in particular active compounds, more particularly such as polyphenols, and/or lead to undesirable reactions.

The dry extract is weighed (g) and the extraction yield is calculated; %=(w/W)×100%, where w is the weight of the dry extract and W the weight of the raw material.

The total phenolics content in the extract may be determined according to the method using Folin-Ciocalteu reagent and/or also by reversed phase HPLC.

The alcoholic extract of *Cinnamon* may comprise at least 30%, in particular at least 35%, and more particularly around 40% (±5) by weight total phenol content equivalent to gallic acid.

The composition for lowering the glycemic index may be under a liquid, a solid, a pasty, a gel or a powder form. In particular this composition may be added on food, more particularly as a liquid or as a powder.

Following another aspect, the invention has for subject matter a food composition comprising a composition for lowering the glycemic index, in particular the glycemic effect of starch, as defined above, in particular in an amount ranging from 0.1 to 5% by weight, more particularly ranging from 0.2 to 2% by weight compared to the total weight of the food composition.

The food composition can be for animal consumption, for example pet food, or for human consumption.

Following an embodiment, the food composition may comprise an amount of *cinnamon* extract as defined above ranging from 0.05 to 5% by weight compared to the total weight of the composition.

The amount of *cinnamon* extract may range from 0.1 to 250 mg/kg, preferably from 10 to 250 mg/kg, in particular from 20 to 200 mg/kg, more particularly from 25 to 180 mg/kg, and even more particularly from 30 to 175 mg/kg of the subject intending to eat the food composition. Following an embodiment, the amount of *cinnamon* extract may range from 0.1 to 20 mg/kg of the subject.

The amount of *cinnamon* extract in the food composition may range from 0.15 to 20 g, in particular from 0.25 to 20 g more particularly from, 0.5 to 18 g, even more particularly from 1 to 15 g.

Thus the amount of coumarin present in the food composition may be lower or equal to 10 ppm by weight, in particular to 5 ppm by weight, more particularly to 3 ppm by weight, and even more particularly to 2 ppm by weight compared to the total weight of the composition.

The food composition may comprise an amount of coumarin such that the amount of delivered to the subject is less than or equal to 0.1 mg/kg/day, in particular less or equal to 0.75 mg/k/day.

The food composition may comprises a starch amount of more than 0.5 g/kg, particularly more than 1 g/kg of body weight of the subject for which food is intended, in particular an animal or a human being.

Preferentially, when intended for an adult human being of 70 kg, the starch amount may be of around 35 g or more.

For example when intended for an adult human being of 70 kg, the starch amount may be of around 70 g or more.

Thus a food composition intended for:
adult human being may comprise 25 g of starch or more, preferentially 50 g of starch or more, cat may comprise 1 g of starch or more, preferentially 2 g of starch or more, dog may comprise 2.5 g of starch or more, preferentially 5 g of starch or more, etc, furthermore the food composition may comprise at least 10 g of starch, in particular at least 20 g of starch.

The weight ratio *cinnamon* extract/starch may also be of 1/10000 or more, in particular of 1/5000 or more, more particularly of 1/1000 or more and even more particularly of 1/500 or more, furthermore the food composition may comprise at least 10 g of starch, in particular at least 20 g of starch.

Alternatively, the amount of the composition for lowering the glycemic index may come from several food compositions.

The food composition may exhibit a glycemic index lowered by 10% to 30% compared to the equivalent food without the composition.

The glycemic index of the invention may in particular be the glycemic index due to starch.

More particularly, the food composition is taken before or at the beginning of the meal.

Following an embodiment, the food composition is a liquid intended to be drunken before and/or during meal.

The food composition may be under a liquid, a solid or a powder form.

The food composition, in particular comprising starch, more particularly in amount as disclosed above, may be bread, pastries, pasta product, dough, flour, rice, product derived from potatoes, appetizers, for example crisps, chewing gums, sweets and/or a drink.

The food composition or the composition for lowering the glycemic index, in particular without starch, may be a sauce, appetizers, sweets, a drink and/or a seasoning.

Following an embodiment, the composition for lowering the glycemic index and the food composition is not intended as medicaments, in particular treating diabetes.

More particularly theses compositions are not intended to be used for persons having declared diabetes.

However, these compositions may be used to help to lose weight and/or to decrease the risks to declare some diseases such as diabetes.

Following still another aspect, the invention has for subject matter the use of a composition for lowering the glycemic index of a food composition or of a food composition as defined above as a glycemic index lowering agent, in particular when combined with a meal comprising starch in an amount of at least 1 g/kg, preferably at least 0.5 g/kg of body weight of the subject intending eating, for example 50 g of starch, preferably 25 g of starch.

The composition for lowering the glycemic index of a food composition or the food composition as defined above may be taken prior, in particular less than 10 minutes, to the meal or taken during the meal, in particular during the first 5 minutes of the meal. Following yet another aspect, the invention has for subject matter a diet comprising taking a food composition or a food composition as defined above prior or at the same time than the meal or at least 3 times a day a composition for lowering the glycemic index. The diet may be intended for losing weight.

The invention also concerns an extract or a composition according to the invention for use as a glycemic index lowering agent, or for use as a weight management agent or for use as satiety regulation agent, or ofr use as a workout supplement.

The invention also concerns the use of an extract or a composition according to the invention for the manufacture of an index lowering agent for prevention of hyperglycemia in a subject, particularly in animals or humans. In such case, the amount of extract used alone or in the composition ranges from 0.1 to 250 mg/kg of the subject, preferably from 10 to 250 mg/kg of the subject, more preferably amount of extract ranges from 30 to 175 mg/kg of the subject. In a preferred embodiment, the amount of extract used alone or in composition ranges from 0.1 to 20 mg/kg of the subject.

The invention also concerns the use of an extract or a composition according to the invention to even sugar release before or during a physical exercise.

Thus the invention also concerns the use of an extract or a composition according to the invention to improve a physical performance.

The index lowering agent is advantageously taken before or at the beginning of a meal, particularly between 10 minutes prior beginning of a meal or during the first 5 minutes of a meal.

The invention also concerns the extract of the invention for its use in the prevention and or treatment of metabolic syndrome, diabetes and/or obesity.

It also concerns the use of an extract or a composition of the invention for the manufacture of a medicament for the treatment of metabolic syndrome, diabetes and/or obesity.

Indeed, the extract or composition of the invention may be used independently for cosmetic purpose and for therapeutic purpose. Both uses are distinct based on the subject intended to be ingesting the extract/composition.

For healthy subject, the purpose of ingesting the extract or composition of the invention, is to control its body shape, avoid unnecessary feelings of hunger, and finally improve his sensations of wellbeing, independently from any risk of developing a metabolic disease.

For athletes, the purpose of ingesting the extract or composition of the invention is to even the sugar release of carbohydrate food, so to avoid blood sugar variations, particularly blood sugar drop or hyperglicemia known to impact physical performance. On the other hand, subjects at risk of developing or having developed metabolic syndrome and/or diabetes and/or obesity, will take the extract/composition of the invention to prevent the development of the diseases and side effects due to elevated glycaemia.

The invention also concerns a method to avoid sugar drop in a subject in need thereof comprising: administering to said subject an effective amount of extract of the invention, wherein:
said effective amount of extract is taken before or at the beginning of the meal; and
said meal comprises starch in an amount of at least 0.5 g/kg of bodyweight of the subject intending to eat the meal; and
said effective amount of extract ranges from 0.1 to 250 mg/kg of the subject intending to eat the meal.

The invention also concerns a method to avoid sugar drop in a subject in need thereof comprising: administering to said subject an effective amount of extract of the invention, wherein:
said effective amount of extract is taken before or at the beginning of the meal; and
said meal comprises starch in an amount of at least 1 g/kg of bodyweight of the subject intending to eat the meal; and
said effective amount of extract ranges from 10 to 250 mg/kg of the subject intending to eat the meal.

The invention also concerns a method for regulating satiety in a subject in need thereof comprising: administering to said subject an effective amount of extract of the invention, wherein:
- said effective amount of extract is taken before or at the beginning of the meal; and
- said meal comprises starch in an amount of at least 1 g/kg of bodyweight of the subject intending to eat the meal; and
- said effective amount of extract ranges from 10 to 250 mg/kg of the subject intending to eat the meal.

The invention also concerns a method for regulating satiety in a subject in need thereof comprising: administering to said subject an effective amount of extract of the invention, wherein:
- said effective amount of extract is taken before or at the beginning of the meal; and
- said meal comprises starch in an amount of at least 0.5 g/kg of bodyweight of the subject intending to eat the meal; and
- said effective amount of extract ranges from 0.1 to 250 mg/kg of the subject intending to eat the meal.

The invention also concerns a method for preventing or reducing hyperglycaemia in a subject in need thereof comprising: administering to said subject an effective amount of an extract of the invention, wherein
- said effective amount of extract is taken before or at the beginning of the meal; and
- said meal comprises starch in an amount of at least 1 g/kg of bodyweight of the subject intending to eat the meal; and
- said effective amount of extract ranges from 10 to 250 mg/kg of the subject intending to eat the meal.

The invention also concerns a method for preventing or reducing hyperglycaemia in a subject in need thereof comprising: administering to said subject an effective amount of an extract of the invention, wherein
- said effective amount of extract is taken before or at the beginning of the meal; and
- said meal comprises starch in an amount of at least 0.5 g/kg of bodyweight of the subject intending to eat the meal; and
- said effective amount of extract ranges from 0.1 to 250 mg/kg of the subject intending to eat the meal.

The invention also concerns a method for preventing obesity or diabetes in a subject in need thereof comprising: administering to said subject an effective amount of an extract of the invention, wherein
- said effective amount of extract is taken before or at the beginning of the meal; and
- said meal comprises starch in an amount of at least 1 g/kg of bodyweight of the subject intending to eat the meal; and
- said effective amount of extract ranges from 10 to 250 mg/kg of the subject intending to eat the meal.

The invention also concerns a method for preventing obesity or diabetes in a subject in need thereof comprising: administering to said subject an effective amount of an extract of the invention, wherein
- said effective amount of extract is taken before or at the beginning of the meal; and
- said meal comprises starch in an amount of at least 0.5 g/kg of bodyweight of the subject intending to eat the meal; and
- said effective amount of extract ranges from 0.1 to 250 mg/kg of the subject intending to eat the meal.

The invention also concerns a method for reducing glycemic index of a food, said method comprising adding to said food an extract of the invention, particularly in a food comprising starch wherein the ratio extract/starch is of 1/30 or more.

The invention also concerns a diet comprising an oral taking of an extract and/or a composition of the invention at least 3 times a day, particularly prior to or at the same time as a meal The examples are aiming to illustrate the invention.

Figure 1:
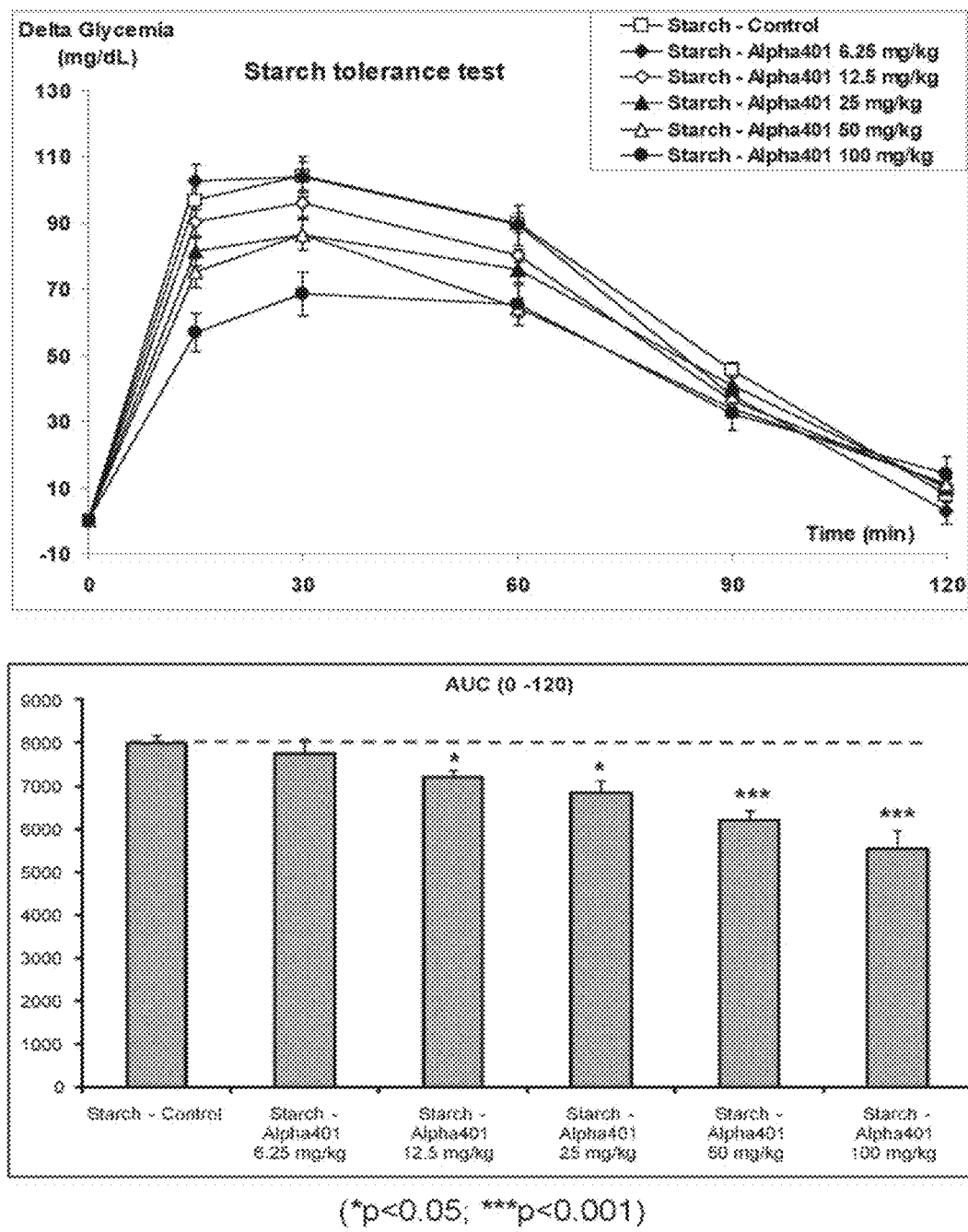
FIG. 1 shows the effect of the *cinnamon* extract on the glycemic index of starch.

FIG. 3 exhibits the effect of *cinnamon* extract and amount of starch ingested on the glycemic index of starch.

FIG. 4 shows the effect of the *cinnamon* extract on the glycemic index of starch and on glucose.

FIG. 5 presents the effect of the *cinnamon* extract on the insulinic response to starch.

FIG. 6 exhibits the effect of the *cinnamon* extract on digestion enzymes: alpha-glucosidase, alpha-amylase, and lipase.

FIG. 7 demonstrates that using high temperature during the process reduces the effect of the *cinnamon* extract on digestion enzymes and on glycemic response to starch.

FIG. 8 presents the effect of the *cinnamon* extract incorporated in food matrixes.

EXAMPLES

Example 1: Preparation of a *Cinnamon* Extract

The *cinnamon* extract was prepared according to the following steps:
- contacting dried milled *cinnamon cinnamomum zeylanicum* bark with 10 times their weight of a 1/1 weight ratio ethanol-water mixture and agitating for 2 hours at a temperature of 50° C., the solids are filtered out and the alcoholic extract is collected,
- the remaining wet solids are washed by stirring with a 1/1 weight ratio ethanol-water mixture, with a volume corresponding to 10 times the weight of the dry solids, for 30 minutes,
- the solid are filtered out and the alcoholic extract collected,
- the extraction solutions are combined and left for decantation or filtered to remove non-soluble residues,
- the water and ethanol are evaporated under vacuum, leading to a brown syrup, the concentrate is then frozen for lyophilisation, and
- the dry *cinnamon* extract is recovered.

The *cinnamon* extract is named Alpha-401.

Example 2: Preparation of a *Cinnamon* Extract

The *cinnamon* extract was prepared according to the following steps:
- contacting dried milled *cinnamon cinnamomum zeylanicum* bark with 7 times their weight of a 1/1 volume ratio ethanol-water mixture and agitating for 2 hours at a temperature of 50° C., the solids are filtered out and the alcoholic extract is collected,
- the remaining wet solids are washed by stirring with a 1/1 volume ratio ethanol-water mixture, with a volume corresponding to minimum of 2 times the weight of the dry solids, for a minimum of 30 minutes, the solid are filtered out and the alcoholic extract collected, the extraction solutions are combined and left for decantation or filtered to remove non-soluble residues, the water and ethanol are evaporated under vacuum, leading to a brown syrup, the concentrate is then frozen for lyophilisation or using a vacuum oven at 50° C., and the dry *cinnamon* extract is recovered.

The *cinnamon* extract is named Alpha-401.

Example 3: Dose Effect in Rats

Six-week old Wistar rats (Janvier Laboratories, France) weighing around 250 g were used for the experiment. One day before the test, rats were randomly assigned to the different experimental groups (8 animals per group) according to their body weight values.

Starch tolerance test (STT) was performed by the administration by oral gavage of a 7.5% purified wheat starch solution at 1.5 g/kg or 20 ml/kg of body weight. The actual volume administered to each rat was calculated and adjusted based on the most recent body weight of each animal.

STT onset was between 12 h00 and 13 h00 on animals fasted overnight. Blood samples (one drop) were collected via the tail vein for glucose determination using a hand-held glucometer (OneTouch Ultra 2, LifeScan) before and 15, 30, 60, and 120 min after starch administration.

In this experiment, the effect of starch alone and starch containing escalating doses of an alcoholic extract of *cinnamomum zeylanicum* (named Alpha-401): 6.25, 12.5, 25, 50, and 100 mg/kg of body weight were compared.

The FIG. 1 represents mean values+/− standard error of the mean (sem; n=8) and shows that the alcoholic extract of *cinnamomum zeylanicum* reduced the glycemic index of starch in a dose-dependent manner. On the graph representing the area under the curve (AUC) between 0 and 120 min, this effect is significant from 12.5 mg/kg of body weight (t-test $p<0.05$).

Example 4: Comparison with Aqueous Extracts

The protocol was the same than Example 2.

In this experiment the effect of alcoholic and aqueous *cinnamon* extracts mixed to starch at the dose of 50 mg/kg of body weight were compared. The aqueous extracts are commercial extracts.

Figure 2:
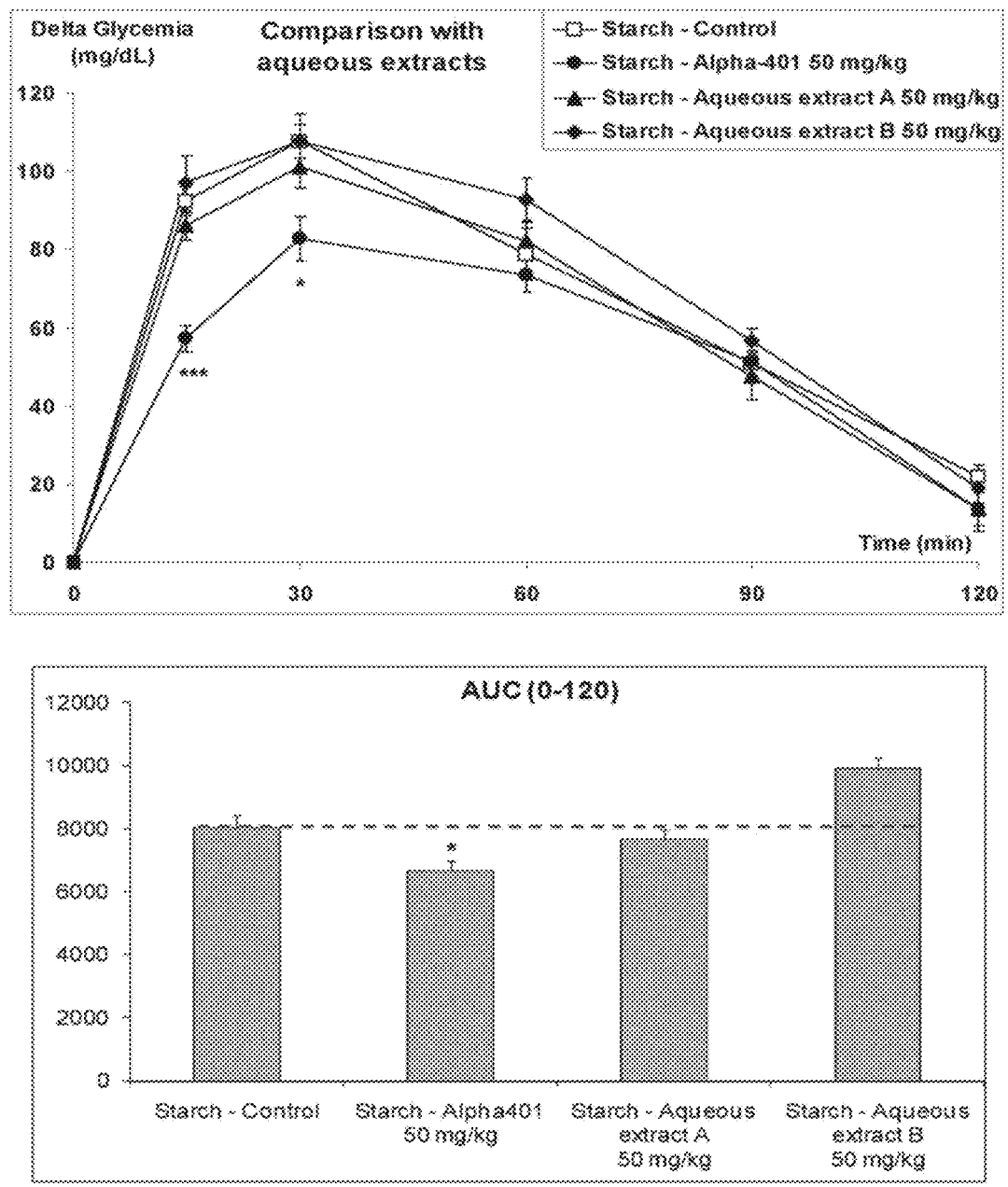
FIG. 2 shows the effect of ethanol and water *cinnamon* extracts on the the glycemic index of starch.

The FIG. 2 shows that two different aqueous extracts presented no effect on the glycemic index of starch. In the same conditions, the alcoholic extract named Alpha-401 (from Example 1) significantly reduced the peak of glycemia at 15 and 30 min (t-test $p<0.001$ and $p<0.05$, respectively) and the AUC between 0 and 120 min (t-test $p<0.05$). This shows the extract according to the invention is having an effect on glycemic index of starch, whereas a water extract has no effect on glycemic index of starch.

Example 5: Effect Dependant of the Quantity of Starch

The protocol was the same than for Example 2 at the difference that 3 different quantities of starch were given to the rats: 1.5, 1, and 0.5 g/kg of body weight.

Then, the effect of an alcoholic extract of *cinnamomum zeylanicum* (named Alpha-401) given at the dose of 50 mg/kg of body weight on the glycemia induced by the digestion of different amount of starch were compared.

The FIG. 3 shows that an alcoholic extract of *cinnamomum zeylanicum* decreased the glycemic index of 1.5 g/kg of body weight of starch in normal rats but when the amount of starch is reduced to 1 or 0.5 mg/kg of body weight this effect is lost. Thus, the effect of *cinnamon* extract on the glycemic index of starch is depending on the quantity of ingested starch.

Example 6: Specific Effect on Starch Versus Glucose

The protocol was the same than for Example 2, at the difference that starch or glucose were given to the animals. Then, the effect of an alcoholic extract of *cinnamomum zeylanicum* (named Alpha-401) given at the dose of 50 and 100 mg/kg of body weight on the glycemia induced by the ingestion of starch and glucose were compared.

The FIG. 4 shows that an alcoholic extract of *cinnamomum zeylanicum* decreased the glycemic index of starch in a dose-dependent manner whereas, in the same conditions, it presented no effect on the glycemia induced by the ingestion of pure glucose (glucose tolerance). This example suggests that the main effect of *cinnamon* extract is done through a reduction of starch digestion.

Example 7: Effect of the *Cinnamon* Extract (Alpha-401) on the Insulinic Response to Starch in Rats The protocol was the same than Example 2, at the difference that only the dose at 50 mg/kg was tested and blood samples were connected to measure insulin levels using an ELISA kit (Ultrasensitive Mouse Insulin ELISA, Mercodia).

The FIG. 5 shows that the *cinnamon* extract Alpha-401 significantly reduced the glycemic response to starch but also reduced the insulinic response to starch. Then, this extract reduced glycemic index of starch without stimulating insulin secretion. On the contrary, the *cinnamon* extract put the pancreas at rest.

Example 8: Effect of the *Cinnamon* Extract (Alpha-401) on Digestion Enzymes

Alpha-glucosidase activity was assayed as follow: 50 µL of the solutions to be tested containing the inhibitors or distilled water (used as control) were added to 100 µL of the enzymatic solution consisting of 1 U/mL of *Saccharomyces cerevisiae* alpha-glucosidase (Sigma-Aldrich) in 50 mM phosphate buffer saline at pH6.9 and pre-incubated during 10 min at room temperature. 50 µL of substrate solution, consisting of 5 mM p-nitrophenyl-alpha-D-glucopyranoside (PNP-G; Sigma-Aldrich) in 50 mM phosphate buffer saline at pH6.9, was added and the mixture was incubated during 5 min at room temperature. The reaction was stopped by the addition of a solution of sodium carbonate 100 mM and the absorbance read at 405 nm. The assay was run in triplicates. The anti-diabetic drug acarbose was used as positive control.

The FIG. 6 shows that the *cinnamon* extract Alpha-401 inhibits alpha-glucosidase activity with an IC50 of 10 µg/mL.

Alpha-amylase activity was assayed using the Enzymatic assay of alpha-amylase inhibitor (Sigma-Aldrich) using alpha-amylase from porcine pancreas and starch from potato. The assay was run in triplicates. The anti-diabetic drug acarbose was used as positive control.

The FIG. 6 shows that the *cinnamon* extract Alpha-401 inhibits alpha-amylase activity with an IC50 of 23 µg/mL.

Lipase activity was assayed as follow: 25 µL of the solutions to be tested containing the inhibitors or distilled water (used as control) were added to 25 µL of the enzymatic solution consisting of 1 mg/mL of lipase from porcine pancreas (Sigma-Aldrich) in distilled water and pre-incubated during 5 min at room temperature. 50 µL of substrate solution, consisting of 0.1 mM 4-Methylumbelliferyl oleate (MUO; Sigma-Aldrich) in Dulbecco's phosphate buffer saline, was added and the mixture was incubated during 20 min at room temperature. The reaction was stopped by the addition of a solution of sodium citrate 100 mM and the luminofluorescence was read at 320 nm stimulation and 450 nm emission wavelengths. The assay was run in triplicates.

The FIG. 6 shows that the *cinnamon* extract Alpha-401 inhibits lipase activity with an IC50 of 44 µg/mL.

Example 9: Importance of the Temperature Used During the Extraction Process on the Efficacy of the *Cinnamon* Extracts The protocols were the same than for Example 2 for starch tolerance test and than for Example 7 for the alpha-glucosidase test.

Sample Alpha-401 50° C. and Alpha-401 60° C. were dried at 50 and 60° C., respectively, during the extraction process.

The FIG. 7 shows that an extraction process using excessive temperature abolishes in vivo the effect of *cinnamon* extract on the reduction of glycemic response to starch and reduces in vitro the inhibition effect of *cinnamon* extract on alpha-glucosidase activity. This example demonstrates that high temperatures during the extraction process reduce the efficacy of *cinnamon* extract on starch glycemic index.

Example 10: Effect of the *Cinnamon* Extract (Alpha-401) Incorporated in Food Matrixes on the Glycemic Response in Rats The protocol was the same than Example 2, at the difference that the *cinnamon* extract was incorporated in food matrixes at different levels (0.5 to 2%). The formulated foods were then put in suspension to be given to the rats.

For the bakery applications, breads were made by a baker following the regular process of confectioning and cooking but by incorporating in the pastry different amounts of *cinnamon* extract. Then, suspensions of bread were given to the rat at the dose of 1.6 g of bread/kg of body weight. The FIG. 8 shows that the *cinnamon* extract dose-dependently reduced the glycemic index of bread. This effect is already significant at an incorporation rate of 0.5%.

For pet food applications, a dog food diet was supplemented with 2% of the *cinnamon* extract Alpha-401, put in suspension and given to rats at 3 g of dog food/kg of body weight. The FIG. 8 demonstrates that the *cinnamon* extract reduced the glycemic response to a pet food diet.

The invention claimed is:

1. A method for reducing glycemic index of food, said method comprising adding to said food an extract of *cinnamomum zeylanicum*, obtained by the process comprising the following steps:
    a) contacting dried milled *cinnamomum zeylanicum* bark with an alcohol based extraction solvent at a temperature of around 50° C.;
    b) filtering out the solids and collecting alcoholic extract;
    c) washing said solids by stirring with an alcohol based extraction solvent;
    d) filtering out the solids and collecting alcoholic extract;
    e) combining said alcoholic extracts;
    f) removing non-soluble residues by decantation, filtration, centrifugation or a combination thereof;
    g) evaporating the solvents from the combination at a temperature inferior or equal to 50° C.; and
    h) recovering a dry extract,
    wherein the extract of *cinnamomum zeylanicum* comprises at least 25% by weight polyphenols, and
    wherein the food comprises starch and the weight ratio *cinnamon* extract/starch is of 1/30 or more.

2. The method for reducing glycemic index of food according to claim 1, said method comprising adding said extract to the food comprising starch, wherein the weight ratio extract/starch is 1/500 or more, 1/1000 or more or 1/10000 or more.

3. The method according to claim 1, wherein the alcohol based extraction solvent further comprises water and the weight ratio water/alcoholic solvent ranges from 5/95 to 50/50.

4. The method according to claim 1, wherein the alcohol based extraction solvent further comprises water and the weight ratio water/alcoholic solvent is 50/50.

5. The method according to claim 1, wherein the alcohol based solvent is chosen from methanol, ethanol, n-propanol, iso-propanol, 2-butanol, and combination thereof.

6. The method according to claim 5, wherein the solvent is ethanol.

7. The method according to claim 6, wherein the solvent further comprises water and the weight ratio water/ethanol is 50/50.

8. The method according to claim 1, wherein steps a) and b) are repeated using said solvent extract obtained in step b) and a new batch of dried *cinnamomum zeylanicum*.

9. The method according to claim 1, wherein steps a) and b) are repeated using said solvent extract obtained in step b) in successive batches of dried *cinnamomum zeylanicum* to obtain saturation of the solvent with the extract.

10. The method according to claim 1, wherein step a) is performed for 1 to 5 hours.

11. The method according to claim 10, wherein step a) is performed for at least 2 hours.

12. A method for producing a food product with a reduced glycemic index, said method comprising reducing the glycemic index of food with the method of claim 1 and recovering said food product.

* * * * *